United States Patent
Kawasaki et al.

(10) Patent No.: US 7,358,404 B2
(45) Date of Patent: Apr. 15, 2008

(54) PROCESS FOR PRODUCING ALCOHOL

(75) Inventors: Hiroki Kawasaki, Okayama (JP); Yuichi Fujita, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/144,590

(22) Filed: Jun. 6, 2005

(65) Prior Publication Data

US 2005/0283030 A1 Dec. 22, 2005

Related U.S. Application Data

(63) Continuation of application No. PCT/JP03/14840, filed on Nov. 20, 2003.

(30) Foreign Application Priority Data

Dec. 4, 2002 (JP) ............... P. 2002-352761

(51) Int. Cl.
C07C 29/14 (2006.01)
(52) U.S. Cl. ........................ 568/880
(58) Field of Classification Search ........... 568/880
See application file for complete search history.

(56) References Cited

U.S. PATENT DOCUMENTS 4,138,588 A 2/1979 Tummes et al.

FOREIGN PATENT DOCUMENTS

| JP | 2-164837 | | 6/1990 |
|----|----------|---|--------|
| JP | 02164837 A | * | 6/1990 |
| JP | 02164837 A2 | * | 6/1990 |
| JP | 6-122638 | | 5/1994 |

OTHER PUBLICATIONS

U.S. Appl. No. 11/144,590, filed Jun. 6, 2005, Kawasaki et al.
U.S. Appl. No. 11/144,621, filed Jun. 6, 2005, Kawasaki et al.

* cited by examiner

Primary Examiner—Yvonne Eyler
Assistant Examiner—Kellette Gale
(74) Attorney, Agent, or Firm—Oblon, Spivak, McClelland, Maier & Neustadt, P.C.

(57) ABSTRACT

It is an object of the present invention to obtain a highly pure alcohol by reducing the aldehyde concentration in the product alcohol efficiently and inexpensively.

The invention relates to a process for producing an alcohol including hydrogenating an aldehyde and subjecting the resultant product to distillation/purification, wherein a total amount of oxygen introduced into the distillation/purification step is 0.0034 mol/s or less of oxygen per 1 kg/s of the product alcohol.

14 Claims, 2 Drawing Sheets

PROCESS FOR PRODUCING ALCOHOL

CROSS REFERENCES TO RELATED APPLICATIONS

This application is a continuation of International Patent Application No. PCT/JP03/14840, filed on Nov. 20, 2003, and claims priority to Japanese Patent Application No. 2002-352761, filed on Dec. 4, 2002.

TECHNICAL FIELD

The present invention relates to a process for producing an alcohol. More specifically, it relates to a process for producing an alcohol comprising hydrogenating an aldehyde and purifying the product, wherein an aldehyde concentration contained in the product alcohol is remarkably reduced than before.

BACKGROUND ART

As a process for producing an alcohol, a method of obtaining a saturated alcohol by hydrogenating an aldehyde and purifying the product is hitherto known and has been commercialized worldwide. For example, with regard to saturated aldehydes, butyraldehyde can be hydrogenated to afford butanol and nonyl aldehyde can be hydrogenated to afford nonanol, and with regard to unsaturated aldehyde, 2-ethylhexenal can be hydrogenated to afford 2-ethylhexanol, 2-propylheptenal can be hydrogenated to afford 2-propylheptanol, and decenal can be hydrogenated to afford decanol.

As the mode of the hydrogenation reaction, it is common to use a reactor, inside of which is usually packed with a nickel-based or cooper-based solid hydrogenation catalyst. There are a mode where a starting aldehyde is vaporized to carrying out the reaction in a vapor phase and a mode where a starting aldehyde is introduced as a liquid into a reactor to carrying out in a liquid phase.

However, regardless of the catalyst species and the reaction mode of vapor phase/liquid phase, there are problems that esterification, acetalization, etherification, and the like occur as undesirable side reactions to lower the selectivity of the reaction in any of the conventional reaction processes and also a satisfactory product alcohol cannot be obtained unless these by-products are separated/removed by distillation operation or the like for purification in subsequent step(s).

As the purification/distillation method of the above crude alcohol, the following methods have been proposed, for example.

The first method is a method of separating low-boiling products in a first column, then separating the alcohol from high-boiling products by distillation to obtain the alcohol product as a distillate from the column top by controlling column top pressure in the second column, and recovering useful products in high-boiling components by controlling the column top pressure in the third column (3-column mode).

Specifically, in Patent Document 1 (JP-B-49-11365), there is described a method wherein purified 2-ethylhexanol is obtained by operating the second column under the conditions of a top pressure of 200 to 800 mmHg and an alcohol content in the bottom of 50 wt % or more and by operating the third column under the condition of a top pressure of 70 to 300 mmHg in the above 3-column mode.

Moreover, there is also known a method wherein the first column is carried out in two steps in the above 3-column mode (4-column mode), i.e., a method wherein low-boiling products are separated by distillation in the first column; then the product alcohol is distilled in the second column; the bottom liquid is further treated to concentrate and separate high-boiling products from the bottom in the third column and then an effective component is recovered by distillation; and the low-boiling products separated in the first column are further concentrated and separated by distillation in the fourth column and an effective component is recovered from the bottom.

Additionally, in order to avoid contamination of the alcohol product distilled from the column top with low-boiling products formed by thermal decomposition of the high-boiling components, particularly acetal components, ether components, and the like in the bottom liquid in the above second column from which the product alcohol is obtained, there is also known a method wherein high-boiling components are separated in the first column, a fraction containing low-boiling components and the alcohol and containing substantially no high-boiling components is distilled from the column top, the fraction is fed to the second column, the low-boiling components are separated from the alcohol, and a fraction containing the low-boiling components as main components is distilled from the column top, while purified alcohol is distilled as a side cut (cf. Patent Document 2).

Furthermore, in the above 2-column mode, there is disclosed a method wherein the high-boiling components are positively thermally cracked and the high-boiling components are recovered as effective component(s) by maintaining the bottom temperature to the value calculated from a prescribed equation or a higher value thereof and the concentration of the high-boiling components in the bottom liquid to 30 wt % or more in the first column from which the high-boiling components are separated (cf. Patent Document 3).

On the other hand, in general, since the product alcohol is frequently used mainly as a plasticizer for resins such as vinyl chloride, an extremely high purity is required and a little coloring, i.e., a little degree of coloring in the sulfuric acid coloring test is required, the test being conducted by heating a sample together with sulfuric acid and then measuring the degree of coloring.

As a component extremely strongly affecting the above sulfuric acid coloring test or the like, an aldehyde may be mentioned. This is because an aldehyde is an unsaturated hydrocarbon. Therefore, the concentration of the aldehyde contained in the product alcohol is one of the most important items for quality of the product alcohol and is desirably reduced.

However, relatively a large amount of the aldehyde is contained in the product alcohol obtained by any of the above precedent methods and thus the product is not thoroughly satisfactory. However, in the above precedent technologies, the concentration of the aldehyde contained in the product alcohol is not at all focused and hence no method for lowering the concentration is disclosed. This may be attributed to the fact that the following can be easily supposed for those skilled in the art when they consider based on common knowledge of chemical engineering without particular disclosed technology.

That is, as methods for reducing the concentration of the aldehyde contained in the product alcohol, there may be considered 1) a method of reducing the amount of unreacted aldehyde to be introduced into the purification system by increasing the conversion rate of the aldehyde into the alcohol in the hydrogenation reaction; 2) a method of increasing the degree of separation of the aldehyde as a low-boiling component by increase of the plate number of the distillation column, increase of reflux ratio, or the like in the step of separating low-boiling components in the purification system; and the like method.

Also, in the actual commercial running, it is supposed that the maintenance of the quality of the product alcohol, i.e., the maintenance of the concentration of the aldehyde contained to a standard value or a lower value thereof may be attempted by the following methods: reduction of the amount of unreacted aldehyde to be introduced into the purification system by changing running conditions such as reaction temperature and the like to suppress the decrease of conversion rate of the aldehyde, the decrease being induced with the decrease of activity of the hydrogenation catalyst with the passage of time (i.e., the method of the above 1)) or increase of the separation efficiency of the aldehyde by increasing the reflux amount or the distillate amount in the low-boiling component-separating column in the purification system (i.e., the method of the above 2)).

However, currently it is very difficult to obtain an alcohol having a low aldehyde concentration.

On the other hand, in the purification/distillation of $C_3$-$C_{10}$ alcohols, it is confirmed that corresponding aldehydes are formed by heat load at the bottom part of the distillation column and a method of distillation in the presence of an alkali metal hydroxide is disclosed as a suppressing means (cf. Patent Document 4). However, in this method, there is a problem that an additional facility for adding the alkali metal hydroxide is necessary and it is impossible to deny a possibility of contamination of the additive into the product alcohol

[Patent Document 1] JP-B-49-11365
[Patent Document 2] JP-A-6-122638
[Patent Document 3] JP-A-7-278032
[Patent Document 4] JP-T-11-500437

DISCLOSURE OF THE INVENTION

In order to reduce the concentration of the aldehyde contained, the present inventors have attempted various ways of operational adjustment in commercial running for many years using the aforementioned chemical engineering techniques. However, even when the conversion rate is increased in the hydrogenation reaction or even when the separation efficiency of the low-boiling components in the low-boiling component-separation column which is a distillation column for separating the aldehyde from the product alcohol in the purification system, they have experienced hardship that the aldehyde concentration in the product alcohol cannot be reduced to a specific value or a lower value thereof.

The product quality should be maintained as a matter of first priority and hence the aldehyde concentration in the product alcohol should be maintained at a predetermined low level. As operational adjustment for the purpose, change of reaction conditions such as change of the reaction temperature to a higher temperature side is necessary for the purpose of increasing the conversion rate of the aldehyde in the hydrogenation reaction. As a result, since the by-product formation rate of the high-boiling components increases even when the conversion rate of the aldehyde is increased, decrease in an alcohol yield and increase in purification/separation costs for the high-boiling components are unavoidable.

Moreover, the countermeasure in the purification system, i.e., the increase of the degree of separation of the low-boiling components by distillation corresponds to the increase in the reflux amount and the distillate amount or the increase in the theoretical plate number of the distillation column, which means increase of running costs for reboiler heat source and facility costs. They result in large increase of burden, which is economically not at all negligible.

Furthermore, even when the aldehyde formation due to heat load is suppressed by lowering the temperature of the bottom of the distillation column to 150° C. or lower through distillation under a pressure lower than atmospheric pressure, the aldehyde concentration in the product alcohol cannot be reduced to less than a specific value or a lower value thereof.

Namely, the invention solves the above problems and an object thereof is to obtain a highly pure alcohol by reducing the aldehyde concentration in the product alcohol efficiently and inexpensively.

As a result of the collection and analysis of plant data in actual commercial running and the precise studies on material balance in the plant for the purpose of the investigation of fundamental measures against the above problems, the inventors have found a surprising fact. That is, they have found that total amount of the aldehyde discharged from the purification system to the outside of the system, i.e., total amount thereof in all efflux streams such as the aldehyde in the product and the aldehyde in a separated low-boiling component stream is always much larger than the amount of the unreacted aldehyde contained in the hydrogenation product introduced into the purification system from the hydrogenation reaction system, although the bottom temperature of the distillation column is low and hence heat load is a little.

This fact indicates that the aldehyde is formed in the purification system by some cause other than heat load. As a result of more precise investigation on the place where it is formed, they have found that, in a system wherein a low-boiling component-separating column is employed as the first column and a product column is employed as the second column, for example, an amount of the aldehyde several times larger than the amount of remaining aldehyde not separated in the first column and introduced from the first column to the second column is contained in the distilled product alcohol of the second column which is the product column, although most of the aldehyde is separated/removed from the column top in the first column which is the low-boiling component-separating column. Namely, they have found that the aldehyde is formed even in the inside of the product column to which a little heat load is applied.

As a result of investigations on the causes of the aldehyde formation in the purification system of the commercial plant from various angles, they have found that, since most part of the process side of the purification/distillation column and ancillary instruments (heat exchanger, reflux drum, pump, etc.) is operated at a pressure of atmospheric pressure or less, there is leakage of outside air into the inside of the column via the gasket and the like of the flange part in the pipe members such as instruments, pipes and valves of the distillation column, heat exchange, drums, and the like although the amount is only minute and they have ascertained that the oxygen in the air causes the dehydrogenation of the alcohol in the inside of the distillation column to form the aldehyde.

They have obtained a finding as a method of forming substantially no aldehyde in the purification system by decreasing the introduction of oxygen, which is a substance of accelerating the aldehyde formation, as far as possible to reduce the amount drastically and thus they have accomplished the invention.

Namely, the gist of the invention lies in the following (1) to (4).

(1) A process for producing an alcohol comprising hydrogenating an aldehyde and subjecting the resultant product to distillation/purification, wherein a total amount of oxygen introduced into the distillation/purification step is 0.0034 mol/s or less of oxygen per 1 kg/s of the product alcohol.

(2) The production process according to the above (1), wherein the aldehyde is an aldehyde having 3 to 10 carbon atoms formed by hydroformylation or a dimerized aldehyde obtained by a further aldol condensation/dehydration reaction of the aldehyde having 3 to 10 carbon atoms formed by hydroformylation.

(3) The production process according to the above (1) or (2), wherein a distillation column is operated under reduced pressure in the distillation step.

(4) The production process according to any one of the above (1) to (3), wherein a conversion rate of the aldehyde is 98% or more in the hydrogenation reaction and concentration of the aldehyde contained in the product alcohol is 0.05 wt % or less.

Figure 1:
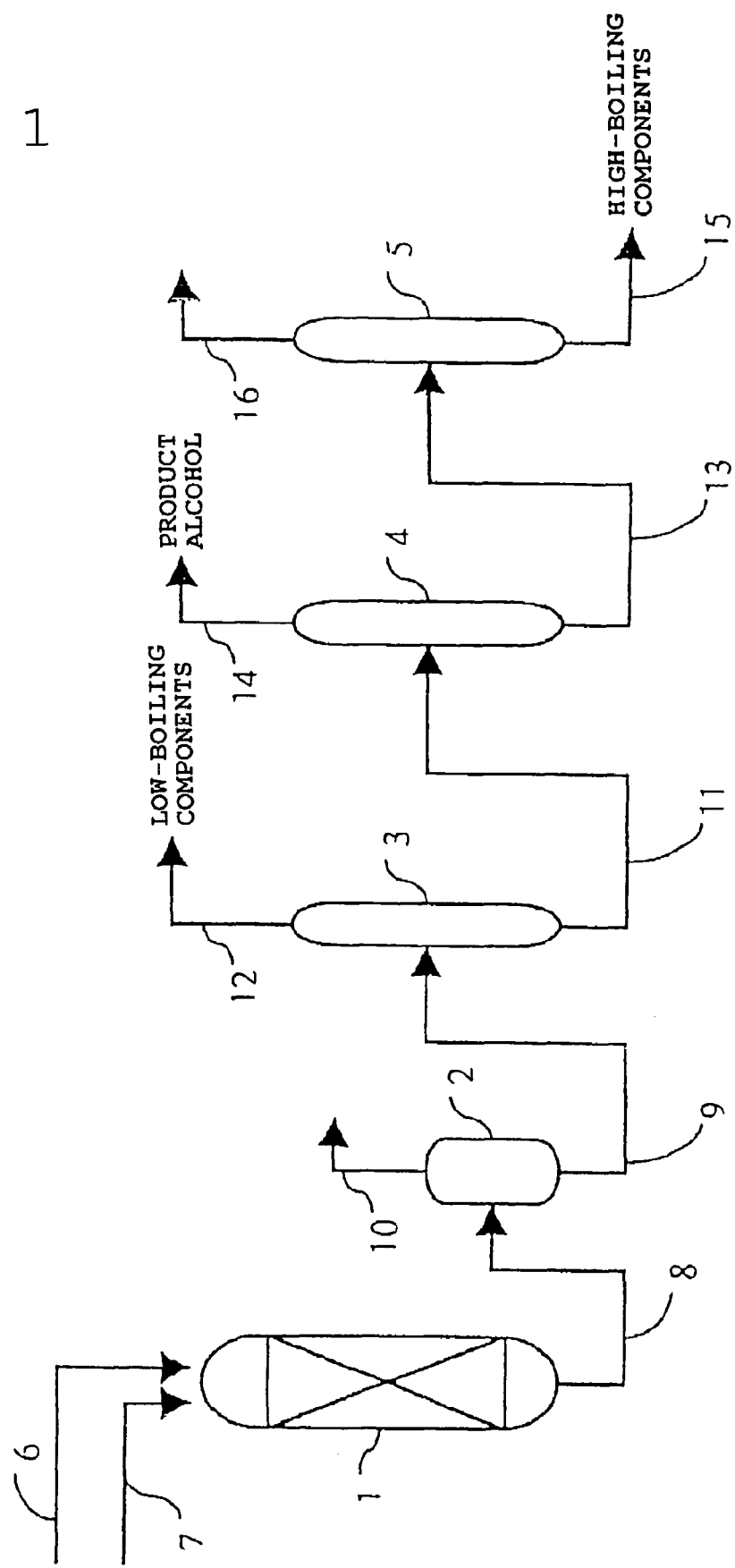
FIG. 1 is a schematic diagram of an alcohol production process.

Incidentally, reference numerals and signs in the drawings are as follows. 1 represents a hydrogenation reactor, 2 represents a gas-liquid separator, 3 represents a low-boiling component-separating distillation column, 4 represents a product-purifying distillation column, 5 represents a high-boiling component-separating distillation column, 21 represents a hydrogenation reactor, 22 represents a gas-liquid separator, 23 represents a first column for separating low-boiling components, 24 represents a second column for taking out a product, 25 represents a third column for recovering an effective component from high-boiling components, and 26 represents a fourth column for recovering an effective component from low-boiling components.

BEST MODE FOR CARRYING OUT THE INVENTION

The following will explain the present invention in further detail.

The aldehyde, which is a starting material for the alcohol, to be used in the invention is not particularly limited and there may be used a saturated aldehyde having at least 3 carbon atoms, usually 3 to 10 carbon atoms, a dimerized unsaturated aldehyde obtained by a further aldol condensation/dehydration reaction thereof, a mixture thereof, or the like.

The saturated aldehyde includes linear and branched aldehydes. Specifically, there may be mentioned propionaldehyde, butyraldehyde, heptyl aldehyde, nonyl aldehyde, undecyl aldehyde, tridecyl aldehyde, hexadecyl aldehyde, heptadecyl aldehyde, and the like.

Moreover, as the unsaturated aldehyde, there may be mentioned 2-ethylhexenal, 2-propylheptenal, decenal, and the like.

Of these, preferred are butyraldehyde, nonyl aldehyde, 2-ethylhexenal, and 2-propylheptenal.

In the invention, the process for producing the aforementioned aldehydes is not limited. For example, in the case of the saturated aldehyde, there may be, for example, mentioned a process for forming an aldehyde by widely commercialized hydroformylation of an olefin, more precisely by hydroformylation of an olefin with oxo gas in the presence of a Group VIII metal complex catalyst having an organophosphorus compound as a ligand, or the like.

Moreover, in the case of the unsaturated aldehyde, it is obtained by an aldol condensation/dehydration reaction of a saturated aldehyde. As the aldol condensation/dehydration reaction, there may be mentioned a method of obtaining an unsaturated aldehyde by dimerizing an aldehyde, which is formed by the above hydroformylation or the like, using an aqueous solution of an alkali such as sodium hydroxide as a catalyst.

In the invention, a commercially available aldehyde can be, of course, employed as the aldehyde.

In the process of the invention, the aforementioned aldehyde is first hydrogenated (hereinafter, sometimes referred to as hydrogenation step).

As the hydrogenation catalyst, any one hitherto known can be employed. For example, there may be mentioned solid hydrogenation catalysts wherein an active component such as nickel, chromium, or copper is supported on a support such as diatomaceous earth or celite. In particular, preferred in the invention is a catalyst wherein nickel and/or chromium are supported as active component(s) on diatomaceous earth as a support. In the hydrogenation reaction of the above aldehyde, the corresponding alcohol is formed by carrying out the reaction usually under the reaction conditions of atmospheric pressure to 150 atm and 40 to 200° C. using the above hydrogenation catalyst.

The reaction may be carried out in a vapor phase by vaporizing a starting aldehyde or may be carried out in a liquid phase by introducing the starting aldehyde as a liquid into a reactor.

In the invention, the conversion rate of the aldehyde in the hydrogenation step is not limited but is desirably in the range of 80 to 99.99%, more preferably 98% or more since the amount of the aldehyde contained in the product alcohol may increase when the conversion rate is too low.

In the invention, in the process on the premise of such a high conversion rate of the aldehyde, it is possible to produce a highly pure alcohol stably without unduly increasing the scale and load of the purification facility.

Then, in the invention, the crude alcohol obtained by hydrogenation is purified (hereinafter, sometimes referred to as purification system or purification step).

In the invention, the purification of the crude alcohol is usually achieved by means of a distillation column. As by-products to be separated, there are high-boiling components such as esters, acetals, and ethers formed by esterification, acetalization, etherification and the like that are side reactions at the hydrogenation reaction, and low-boiling components such as decomposed products thereof, unreacted aldehyde, and isomer alcohols. However, among the ethers, some may behave as low-boiling components with forming azeotropes with alcohols.

In the invention, the distillation is not particularly limited but is usually carried out under atmospheric pressure or reduced pressure, preferably under reduced pressure. The preference is for the purpose of decreasing heat load at the bottom of the distillation column and also lowering the temperature level of the reboiler heat source.

In the invention, the distillation column is not limited and use can be made of a distillation column optionally having a reflux drum, a condenser, a reboiler, and/or a preheater. Of course, the distillation column may have the other ancillary instruments according to need. Moreover, the plate number of the distillation column may be suitably determined.

In the invention, since dissolved gases such as hydrogen, methane, and nitrogen are dissolved in the crude alcohol, it is preferred to separate them prior to the distillation. After the separation of the dissolved gases, the product alcohol is taken out by means of the distillation column. In this connection, in addition to the distillation, the distillation for removing the low-boiling components, the distillation for removing the high-boiling components, and the like distillation may be conducted in combination. Particularly preferably, the distillation for removing the low-boiling components is conducted prior to the distillation for obtaining the alcohol as a final product and the distillation for removing the high-boiling components is conducted after the distillation for obtaining the alcohol.

In the invention, it is indispensable that a total amount of oxygen introduced into the distillation/purification step is 0.0034 mol/s or less of oxygen per 1 kg/s of the product alcohol and the amount is preferably 0.00024 mol/s or less. When the amount of oxygen introduced is too large, the alcohol is oxidized to form the aldehyde in the distillation column and the aldehyde not thoroughly separated by distillation may contaminate the product alcohol, so that there arises a problem that the aldehyde in the product alcohol increases.

The distillation/purification step in the invention means a step from the entrance of the distillation column for purifying the alcohol until the alcohol is obtained as a final product. For example, in a system where a low-boiling component-separating column is used as the first column and a product column is used as the second column, the first column and the second column are included. Moreover, the third column is also included in the case that the alcohol as the final product is recovered in the third column as an effective component from the low-boiling components separated in the first column, and the fourth column is also included in the case that the alcohol as the final product is recovered in the fourth column as an effective component from the high-boiling components separated in the second column (cf. FIG. 2: in FIG. 2, 21 represents a hydrogenation reactor, 22 represents a gas-liquid separator, 23 represents a first column for separating low-boiling components, 24 represents a second column for taking out a product, 25 represents a third column for recovering an effective component from high-boiling components, and 26 represents a fourth column for recovering an effective component from low-boiling components.

Figure 2:
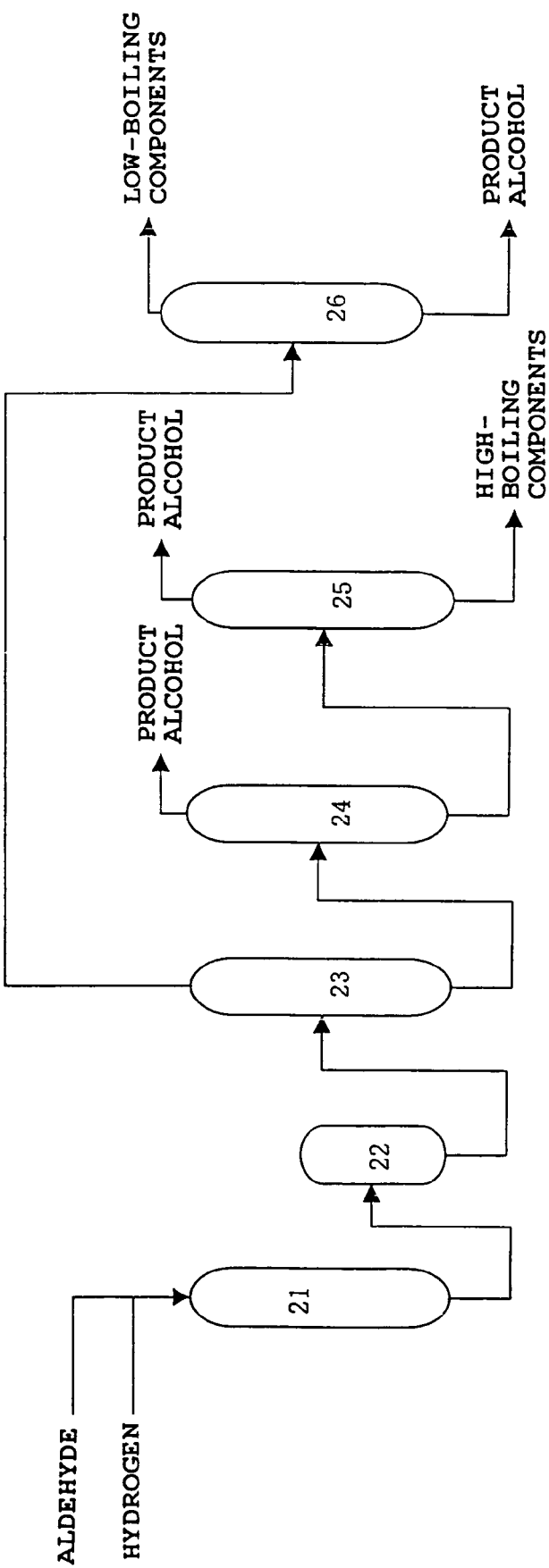
FIG. 2 is a schematic diagram of an alcohol purification process.

For example, in FIG. 2, with regard to the crude alcohol discharged from the hydrogenation reactor 21, in the case of a process where, after the separation of dissolved gases in the gas-liquid separator 22, low-boiling components are separated in the first column 23, high-boiling components are separated in the second column 24 to obtain the alcohol as the final product, the alcohol as the final product is recovered as an effective component in the third column 25 from low-boiling components separated in the first column 23, and the alcohol as the final product is recovered as an effective component in the fourth column 26 from high-boiling components separated in the second column 24, the purification steps in the invention refer to the first column 23, the second column 24, the third column 25, and the fourth column 26.

In the invention, a plurality of the distillation columns may be employed and may possess a reflux drum, a condenser, a reboiler and/or a preheater (hereinafter, sometimes referred to simply as distillation column). In the invention, it is sufficient that the total amount of oxygen introduced into each instrument in the above distillation/purification step is 0.0034 mol/s or less of oxygen per 1 kg/s of the product alcohol.

Incidentally, in the invention, the total amount of oxygen introduced into the distillation/purification step can be calculated, for example, by measuring an oxygen amount through sampling at a drum or tank immediately before the distillation column and multiplying the amount by a flow rate. The amount of oxygen leaked in from the flange parts and valves of the instruments can be confirmed by reducing the pressure in the distillation column to a certain degree of vacuum before its running, allowing to stand it for several hours in a closed state with shutting valves off, and measuring the increase of the pressure during the period of time. Furthermore, in the case of a distillation column using a pressure-reducing apparatus, the amount of oxygen introduced can be also presumed by determining whether the pressure-reducing apparatus works or not, the amount sucked by the pressure-reducing apparatus being set as an air amount corresponding to the amount of oxygen introduced.

Moreover, in the case that there is a possibility that oxygen is introduced through its contamination in the starting gas and starting aldehyde, the sum of the amounts of oxygen introduced is controlled in the produced alcohol so as to be in the range defined in the above. The amount of oxygen introduced into the starting gas and starting aldehyde can be confirmed by sampling the crude alcohol to be fed to the distillation column and analyzing the sample. Specifically, in the case of a gas, the amount can be determined through the analysis by means of an oxygen analyzer or in the case of a liquid, it can be determined by collecting several samples and analyzing them by means of an oxygen analyzer.

Before the start of the distillation facility, it is preferred to test the airtightness of the facility. The method of the test is not particularly limited. As a common method, every instrument or every suitably separated section is blocked with a partitioning board or the like and, after pressurized to about a designed pressure of the instrument with an inert gas such as nitrogen and allowed to stand for a certain period of time, the presence of leakage is confirmed by comparing the pressure in the instrument before and after the standing. Moreover, for the confirmation of leakage at the flange parts and welded parts, it is also possible to confirm the leakage by applying soap water in a pressurized state. In the case that much leakage is observed, measures such as secondary tightening of the flange parts are taken. When the pressurization-standing test is finished, the pressure in the instrument is reduced to around an operating pressure or a lower pressure by means of a pressure-reducing apparatus such as a vacuum pump or an ejector and then it is allowed to stand for a certain period of time. Thereafter, the presence of leakage is confirmed by comparing the pressure in the instrument before and after the standing. As a matter of course, in the case that the temperature is different before and after the standing, it is desirable to conduct correction for temperature. Thus, it is confirmed that the total amount of the air leaked in the distillation columns and ancillary instruments in the whole purification system is equal to or less than the above defined value.

When the amount of the air leaked in is more than the defined value, the flange parts, welded parts, valves, and the like are checked and measures such as secondary tightening of the flange parts are taken.

The following will explain a specific example of the process for producing an alcohol of the invention with reference to FIG. 1.

Hydrogen gas and an aldehyde are fed from the lines 6 and 7 to a hydrogenation reactor 1 packed with a hydrogenation catalyst to carrying out a hydrogenation reaction. The formed liquid is transferred into a gas-liquid separator. 2 though a line 8 and is separated from dissolved gases in the gas-liquid separator 2. The dissolved gases are discharged into the outside of the system through a line 10.

After the separation of the dissolved gases, the formed liquid is transferred through a line 9 into a low-boiling component-separating distillation column 3, where low-boiling components are separated. Passing through a line 12, the separated low-boiling components are typically stored in a tank or the like as a fuel oil and burned, but it is also possible to recover an effective component by further distillation.

The bottom product after the separation of the low-boiling components is fed to a product-purifying distillation column 4 through a line 11 and, after the separation of high-boiling components, a product alcohol is obtained from the top of the distillation column. In this connection, the high-boiling components are transferred into a high-boiling components-separating distillation column 5 together with a product alcohol not separated at the product-purifying distillation column 4 though a line 13 and the high-boiling components are taken out from the bottom of the distillation column through a line 15, while the alcohol is taken out through a line 16.

As above, in the invention, by suppressing the amount of the oxygen introduced into a distillation column to a certain amount or less, a highly pure alcohol having a concentration of the aldehyde contained in the product alcohol of 0.05 wt % or less, preferably 100 ppm or less, more preferably 50 ppm or less can be stably obtained in the process wherein the aldehyde conversion rate in the hydrogenation reaction is 98% or more.

EXAMPLES

The following will explain specific embodiments of the invention in further detail with reference to Examples but the invention is not limited by the following Examples unless it exceeds the gist.

Example 1

Under a nitrogen atmosphere, 100 cc of a 2-ethylhexanol sample was charged into a 200 cc round-bottom flask and a powder obtained by supporting nickel and chromium as active components on diatomaceous earth as a support was added thereto as a hydrogenation catalyst so that catalyst concentration became 14 wt ppm. The temperature was elevated over the period of about 5 minutes and sampling was performed after 0 minute, 10 minutes, 60 minutes, and 150 minutes from the point of time when the temperature reached 140° C., the concentration of 2-ethylhexanal as an aldehyde being analyzed.

The results are shown in Table 1.

Comparative Example 1

This example was carried out in the same manner as in Example 1 except that it was carried out under an air atmosphere.

The results are shown in Table 1.

TABLE 1

| | | Example 1 | Comparative Example 1 |
|---|---|---|---|
| Content of hydrogenation catalyst | | 14 wt ppm | 14 wt ppm |
| Atmosphere | | Nitrogen | Air |
| Temperature | | 140° C. | 140° C. |
| 2-Ethyl-hexanal (wt %) | After 0 minute | 0 | 0 |
| | After 10 minute 1 | 0.0031 | 0.0072 |
| | After 60 minutes | 0.0031 | 0.042 |
| | After 150 minutes | 0.0031 | 0.105 |

From the above Example 1 and Comparative Example 1 described in Table 1, it is revealed that the formation of the aldehyde can be remarkably suppressed by removing the air (oxygen).

Example 2

In a 2-ethylhexanol plant wherein the production capacity of an alcohol was 2.5 t/hour and total of inner solutions of the product distillation column and ancillary instruments thereof of the purification system was 16 m$^3$, at a stage after periodic repair and before startup of the plant, the product column of the purification system in a clean state without any substance to be gasified, such as a process liquid or water in the column, was vacuumed to 100 mmHgA by an ejector after the column had been shut off from the outside to be a closed system. After a while, the ejector was stopped and the column was allowed to stand for 4 hours. It was confirmed that the value of pressure increase in the column after correction for temperature during the period was 12 mmHg. Namely, the amount of oxygen to be introduced into the distillation column was found to be 0.000237 mol/s of oxygen per 1 kg/s of product alcohol.

Thereafter, the plant was started and 2-ethylhexanol was produced using 2-ethylhexanal as a starting material. Incidentally, no oxygen was dissolved in the reaction product liquid fed to the distillation column and all the oxygen introduced into the distillation column was due to the leakage of air. When the product 2-ethylhexanol was analyzed in a stationary state, the concentration of 2-ethylhexanal in the product was always 0.005 wt % or less.

Of the total of the amount of 2-ethylhexanal taken out of the purification system in this case, the ratio of the amount of unreacted 2-ethylhexanal introduced from the hydrogenation reaction system was about 90% or more.

Example 3

In a plant wherein 0.0034 mol/s per 1 kg/s of product alcohol was adopted as a design standard of an ejector, the operation was started in a bad airtight condition without performing the vacuum-standing test as in Example 2. The operation conditions for the hydrogenation reaction and the purification system were basically the same as in Example 2. Since the ejector did work, the amount of the gas sucked by the ejector was equal to or less than the designed value and hence it was confirmed that the amount of the air leaked in was equal to or less than the designed value of 0.0034 mol/s per 1 kg/s of product alcohol, with calculated in terms of oxygen. Incidentally, no oxygen was dissolved in the reaction product liquid fed to the distillation column and all the oxygen introduced into the distillation column was due to the leakage of air.

In this case, the concentration of 2-ethylhexanal in the product increased by 0.05 wt % at the maximum, but it is a sufficient quality as an industrial alcohol.

Of the total of the amount of 2-ethylhexanal taken out of the purification system in this case, the ratio of the amount of unreacted 2-ethylhexanal introduced from the hydrogenation reaction system was about 10% or more.

While the invention has been described in detail and with reference to specific embodiments thereof, it will be apparent to one skilled in the art that various changes and modifications can be made therein without departing from the spirit and scope thereof.

This application is based on a Japanese patent application filed on Dec. 4, 2002 (Application No. 2002-352761), the entire contents thereof being hereby incorporated by reference.

INDUSTRIAL APPLICABILITY

According to the present invention, the aldehyde formation in a purification system can be remarkably reduced and a product alcohol having a high quality can be always produced stably.

The invention claimed is:

1. A process for producing an alcohol, comprising:
   hydrogenating an aldehyde; and
   subjecting the resultant product to distillation/purification;
   wherein:
   subjecting the resultant product to distillation/purification comprises employing a pressure-reducing apparatus to control a total amount of oxygen introduced during distillation/purification to an amount of 0.0034 mol/s or less of oxygen per 1 kg/s of the product alcohol.

2. The process according to claim 1, wherein the aldehyde is an aldehyde having 3 to 10 carbon atoms formed by hydroformylation or a dimerized aldehyde obtained by a further aldol condensation/dehydration reaction of the aldehyde having 3 to 10 carbon atoms formed by hydroformylation.

3. The process according to claim 1, wherein a distillation column is operated under reduced pressure in the distillation step.

4. The process according to claim 1, wherein a conversion rate of the aldehyde is 98% or more in the hydrogenation reaction and concentration of the aldehyde contained in the product alcohol is 0.05 wt % or less.

5. The process according to claim 1, wherein a total amount of oxygen introduced into the distillation/purification step is 0.00024 mol/s or less of oxygen per 1 kg/s of the product alcohol.

6. The process according to claim 2, wherein a total amount of oxygen introduced into the distillation/purification step is 0.00024 mol/s or less of oxygen per 1 kg/s of the product alcohol.

7. The process according to claim 3, wherein a total amount of oxygen introduced into the distillation/purification step is 0.00024 mol/s or less of oxygen per 1 kg/s of the product alcohol.

8. The process according to claim 4, wherein a total amount of oxygen introduced into the distillation/purification step is 0.00024 mol/s or less of oxygen per 1 kg/s of the product alcohol.

9. The process according to claim 1, wherein the concentration of the aldehyde contained in the product alcohol is 100 ppm or less.

10. The process according to claim 9, wherein a total amount of oxygen introduced into the distillation/purification step is 0.00024 mol/s or less of oxygen per 1 kg/s of the product alcohol.

11. The process according to claim 1, wherein the concentration of the aldehyde contained in the product alcohol is 50 ppm or less.

12. The process according to claim 11, wherein a total amount of oxygen introduced into the distillation/purification step is 0.00024 mol/s or less of oxygen per 1 kg/s of the product alcohol.

13. The process according to claim 1, wherein said aldehyde comprises one or more members selected from the group consisting of butyraldehyde, nonylaldehyde, 2-ethylhexenal, 2-propylheptenal, and mixtures thereof.

14. The process according to claim 13, wherein a total amount of oxygen introduced into the distillation/purification step is 0.00024 mol/s or less of oxygen per 1 kg/s of the product alcohol.

* * * * *